United States Patent
Holzhacker

(10) Patent No.: US 9,639,928 B2
(45) Date of Patent: May 2, 2017

(54) METHOD AND DEVICE FOR SIMPLIFYING INFORMATION OBTAINED FROM ELECTRICAL IMPEDANCE TOMOGRAPHY

(71) Applicant: Timpel S.A., São Paulo (BR)

(72) Inventor: Rafael Holzhacker, São Paulo (BR)

(73) Assignee: TIMPEL S.A., São Paulo (BR)

( * ) Notice: Subject to any disclaimer, the term of this patent is extended or adjusted under 35 U.S.C. 154(b) by 0 days.

(21) Appl. No.: 14/441,167

(22) PCT Filed: Nov. 5, 2013

(86) PCT No.: PCT/BR2013/000464
§ 371 (c)(1),
(2) Date: May 6, 2015

(87) PCT Pub. No.: WO2014/071482
PCT Pub. Date: May 15, 2014

(65) Prior Publication Data
US 2015/0287186 A1    Oct. 8, 2015

(30) Foreign Application Priority Data

Nov. 6, 2012    (BR) ..................... 10 2012 028367 0

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0536* (2013.01); *A61B 5/08* (2013.01);
(Continued)

(58) Field of Classification Search
CPC .. A61M 2016/0021; A61M 2016/0036; A61M 2205/075; A61M 2205/502;
(Continued)

(56) References Cited

U.S. PATENT DOCUMENTS 6,678,552 B2 * 1/2004 Pearlman ............. A61B 5/0536
    600/547
6,725,087 B1 * 4/2004 Rubinsky ............... G06Q 50/24
    128/920

(Continued)

FOREIGN PATENT DOCUMENTS

WO    0193760 A1    12/2001
WO    2006012181 A1    2/2006
(Continued)

OTHER PUBLICATIONS

International Search Report for International Application No. PCT/BR2013/000464, mailed Feb. 7, 2014, 7 pages.
(Continued)

*Primary Examiner* — Vu Le
*Assistant Examiner* — Aklilu Woldemariam
(74) *Attorney, Agent, or Firm* — TraskBritt

(57) ABSTRACT

A method and apparatus to simplify information obtained through electrical impedance tomography, the method comprising the steps of data collection through electrical impedance tomography and the respective processing thereof; the application of at least one algorithm to detect conditions, trends and specific events, so as to allow the identification of at least one region of interest as well as the production of an image including at least such region, which can be predefined or defined by the user. The graphical representation of the region of interest can be obtained through the use of a color, texture, figure, contour, etc. The data processed can consist of the impedance values or data derived thereof.

19 Claims, 7 Drawing Sheets

(51) Int. Cl.
  *A61B 5/053* (2006.01)
  *A61B 5/08* (2006.01)
  *A61B 5/00* (2006.01)
  *G06T 7/40* (2017.01)
  *G06T 11/00* (2006.01)

(52) U.S. Cl.
  CPC ............ *A61B 5/7275* (2013.01); *A61B 5/743* (2013.01); *A61B 5/748* (2013.01); *A61B 5/7485* (2013.01); *G06T 7/0081* (2013.01); *G06T 7/0083* (2013.01); *G06T 7/40* (2013.01); *G06T 11/003* (2013.01); *G06K 9/00* (2013.01); *G06T 2207/10072* (2013.01); *G06T 2207/20021* (2013.01); *G06T 2207/30004* (2013.01)

(58) Field of Classification Search
  CPC ........ A61M 2205/584; A61M 2230/65; A61B 5/0536; A61B 5/087; A61B 5/411; A61B 5/1032; A61B 5/08; A61B 5/7275; A61B 5/743; A61B 5/748; A61B 5/7485; A61B 5/044; A61B 5/4869; A61B 5/0422; A61B 5/053; A61B 6/03; G06T 7/0081; G06T 15/08; G06T 2207/30064; G06T 2200/24; G06T 2207/30061; G06T 2207/10072; G06T 7/0083; G06T 2207/20021; G06T 2207/30004; G06T 7/0012; G06T 7/40; G06T 2211/416; G06T 7/602; G06T 9/20; G03H 1/22; G03H 2210/30; A45D 2044/007; A45D 44/005; G06F 19/3481; G01J 3/508; G01N 27/327; G01N 21/21; A61N 1/36521
  USPC ........ 382/128, 129, 130, 131, 132; 600/547, 600/301
  See application file for complete search history.

(56) References Cited

U.S. PATENT DOCUMENTS

| | | | | |
|---|---|---|---|---|
| 6,768,921 B2* | 7/2004 | Organ | ................ | A61B 5/0536 600/300 |
| 7,302,292 B2* | 11/2007 | Ginor | ................ | A61B 5/0536 600/300 |
| 7,435,226 B2 | 10/2008 | Suarez | | |
| 7,907,997 B2* | 3/2011 | Stahmann | ............ | A61B 5/0537 600/528 |
| 8,099,299 B2* | 1/2012 | Sirohey | ................ | G06F 19/321 348/47 |
| 8,103,337 B2* | 1/2012 | Graovac | ............. | A61B 5/0536 345/424 |
| 8,886,291 B2* | 11/2014 | Hartov | ................ | A61B 5/0536 382/128 |
| 2003/0095696 A1* | 5/2003 | Reeves | ................ | G06T 5/20 382/131 |
| 2004/0252870 A1* | 12/2004 | Reeves | ................ | G06T 7/0012 382/128 |
| 2005/0201598 A1* | 9/2005 | Harel | ................ | G06T 7/0012 382/128 |
| 2006/0155577 A1* | 7/2006 | Niemeyer | ............ | G06F 19/321 705/2 |
| 2007/0282200 A1* | 12/2007 | Johnson | ................ | A61B 5/05 600/437 |
| 2008/0080614 A1* | 4/2008 | Munoz | ................ | H04N 7/012 375/240.01 |
| 2008/0205717 A1* | 8/2008 | Reeves | ................ | G06T 7/0012 382/128 |
| 2008/0224688 A1* | 9/2008 | Rubinsky | ............ | A61B 5/05 324/76.77 |
| 2009/0024008 A1 | 1/2009 | Brunner et al. | | |
| 2009/0264791 A1* | 10/2009 | Gregory | ................ | A61B 5/0536 600/547 |
| 2009/0292551 A1* | 11/2009 | Sirohey | ................ | G06F 19/321 705/2 |
| 2010/0027863 A1* | 2/2010 | Venkataraman | ... | A61B 1/00009 382/131 |
| 2010/0228143 A1* | 9/2010 | Teschner | ............ | A61B 5/0536 600/547 |
| 2011/0275538 A1* | 11/2011 | Sonkusale | ........ | G01N 33/4836 506/10 |
| 2012/0070044 A1* | 3/2012 | Avinash | ................ | G06K 9/3233 382/128 |
| 2015/0287186 A1* | 10/2015 | Holzhacker | ........ | A61B 5/0536 382/131 |

FOREIGN PATENT DOCUMENTS

| | | |
|---|---|---|
| WO | 2009042637 A2 | 4/2009 |
| WO | 2012007425 A1 | 1/2012 |

OTHER PUBLICATIONS

Written Opinion of the International Searching Authority for International Application No. PCT/BR2013/000464, mailed Feb. 7, 2014, 8 pages.

International Preliminary Report on Patentability for International Application No. PCT/BR2013/000464, mailed May 12, 2015, 9 pages.

European Supplemental Search Report for European Patent Application No. 13853510.9, dated Jun. 24, 2016, 7 pages.

* cited by examiner

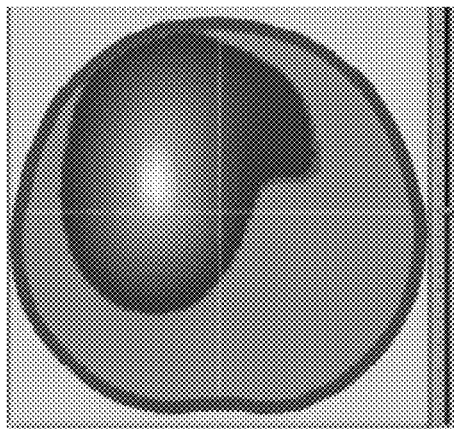 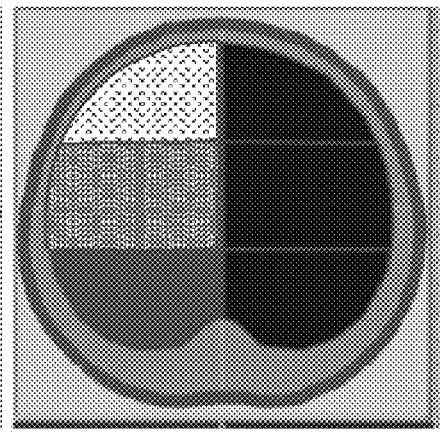
FIG. 6A    FIG. 6B
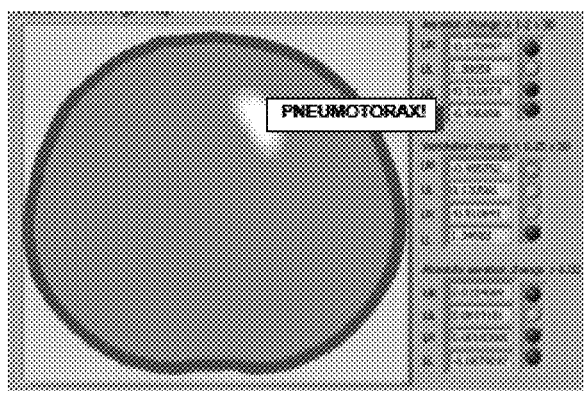 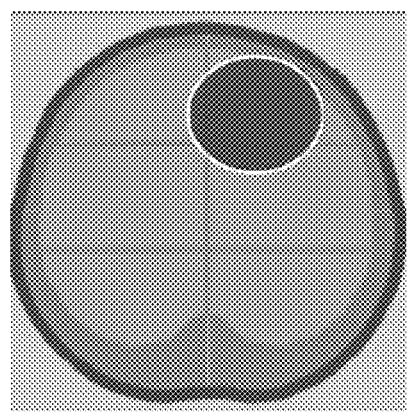
FIG. 7A    FIG. 7B

METHOD AND DEVICE FOR SIMPLIFYING INFORMATION OBTAINED FROM ELECTRICAL IMPEDANCE TOMOGRAPHY

CROSS-REFERENCE TO RELATED APPLICATIONS

This application is a national phase entry under 35 U.S.C. §371 of International Patent Application PCT/BR2013/000464, filed Nov. 5, 2013, designating the United States of America and published as International Patent Publication WO 2014/071482 A1 on May 15, 2014, which claims the benefit under Article 8 of the Patent Cooperation Treaty and under 35 U.S.C. §119(e) to Brazilian Patent Application Serial No. BR 10 2012 028367 0, filed Nov. 6, 2012, the disclosure of each of which is hereby incorporated herein in its entirety by this reference.

TECHNICAL FIELD

This disclosure refers to the field of electrical impedance tomography (EIT) and, more particularly, to the treatment of images so that they may be interpreted in an easier way.

BACKGROUND

Electrical Impedance Tomography (EIT) is a technique for obtaining images that is based on the application of alternating electrical signals whose frequencies range between 10 kHz and 2.5 MHz on a patient's body surface. The device used to this end comprises a plurality of electrodes (e.g., electrodes 1030 in FIG. 10) placed in contact with the skin, which are connected through electric conductors to a processing unit that produces the signal. The method used comprises a plurality of steps in each of which a pair of electrodes is selected for the signal injection, while induced voltages are measured at the electrodes that are not being used for the signal injection. In the following steps, other pairs of electrodes for signal injection are selected, continuing the sequence until all the electrodes of the device are selected, completing an exploration cycle. The induced voltages that were captured by electrodes are submitted to a treatment through a specific software, allowing the production of images that represent ventilation and perfusion phenomena in the body of interest.

One of the great advantages of the Electrical Impedance Tomography over the pneumotachograph, for instance, is that as the EIT generates images, it provides the user regional information of the body under study.

However, in conformity with the prior art, the images are shown in their highest possible resolution, in which each pixel has its corresponding impedance value. Algorithms to filter the noise and improve the image are used, but always seeking to determine the value of each pixel in order to show it in the image.

Despite the effort to develop increasingly more precise EIT devices, a great challenge is still represented by the capacity of interpretation and users' use of the information generated by this device. Even skilled physicists and physiotherapists find the interpretation of these images difficult. This is a limitation for the use of this technology, which, if widely used, would allow a significant increase in the patient survival by allowing the adjustment of ventilator and hemodynamic parameters and appropriate maneuvers.

U.S. Pat. No. 7,435,226, entitled METHOD AND APPARATUS FOR DISPLAYING INFORMATION OBTAINED BY ELECTRICAL IMPEDANCE TOMOGRAPHY DATA, describes various screen modes and suggests graphics and numerical values as a way to achieve data reduction to aid image interpretation. The data used to generate the images are processed in a different manner to calculate and display the graphic and numerical values.

The attempt to show the information of the image in a graphic or numerical format is valid, but it does not improve the image itself that, as said, is the main advantage of EIT. Conversely, construction and multiple graphs, one for each region of interest, involve a higher level of difficulty for the user, instead of facilitating the cognitive effort to interpret the images. This is even more important in those cases in which the space reserved to EIT data is limited, for instance, in EIT modules that use the screen of the device already installed in the Intensive Care Unit, such as a monitor or ventilator, for example.

U.S. Patent Application Publication 2009/0024008, entitled METHOD AND APPARATUS FOR SIMPLIFYING DIAGNOSTIC ASSESSMENT OF A MECHANICALLY VENTILATED PATIENT, requires the collection of parameters of different origin as it builds an illustration of the lung therefrom, which is either increased or decreased depending on the volume and rate of ventilation.

The lung illustration aims at giving the user a qualitative picture of the acquired physiological parameters. Although, at first sight, it looks like an interesting idea, this technology leads to the creation of new graphical elements (images) from a numerical value, requiring users to consider these two types of representation.

International Publication WO 2012/007425, entitled METHOD AND APPARATUS FOR TIME-BASED ANALYSIS OF ELECTRICAL IMPEDANCE TOMOGRAPHY DATA, describes a method and apparatus in which an EIT image comprises one or a plurality of pixels that represent a specific impedance value or even a specific PAT (Pulse Arrival Time) value, calculated for pixels or a set of pixels. Since a plurality of pixels has the same underlying value, it is natural that this set is represented in the same manner. However, this does not solve the problem to simplify the graphical representation, using a set of pixels with different impedance values, presented in a uniform manner, depending on a condition, event or trend identified in this region, composed of this set of pixels.

U.S. Patent Application Publication 2012/0228143, entitled APPARATUS AND METHOD TO DETERMINE FUNCTIONAL LUNG CHARACTERISTICS, describes an apparatus and a method to determine the functional characteristic of the lung, through Electrical Impedance Tomography. From the regions of interest, the ratio between the impedance in this region and the global impedance is calculated for each region, resulting in graphs and indexes that present these ratios. The above-mentioned document does not state that such indexes are represented in the image itself through a uniform representation of the region of interest. On the contrary, it refers to numerical indexes and graphs that do not improve the image itself, involving a higher level of difficulty for the user.

Thus, it is evident that the prior art does not result in a simplification of the image, as it does not provide additional ways to represent or reduce the information.

BRIEF SUMMARY

In view of the foregoing, the object of this disclosure is to provide a method and an apparatus to simplify the interpretation by the user of the images obtained through electrical impedance tomography, making this technology more effectual and liable to be spread.

Another object is to provide a method and an apparatus for the determination of regions of interest.

Another object is to provide a method and an apparatus to provide graphical representations in the image itself, for each region of interest, capable of displaying multiple conditions, events and trends in these regions.

Another object is to provide a method and an apparatus to suggest approaches to correct anomalies and deviations identified in the regions of interest.

GENERAL DESCRIPTION OF THE DISCLOSURE

Both the aforementioned objectives and others are achieved by the disclosure through a method that comprises the following steps:
Data collection through electrical impedance;
Data processing;
Application of at least one algorithm to detect specific conditions, trends or events;
Identification of at least one region of interest, comprising the set of two or more pixels having in common a certain underlying condition, event or trend.

In conformity with another characteristic of the disclosure, the method comprises the following additional steps:
Identification of at least one graphical representation comprising at least a set of two or more pixels that configure a region of interest (ROI);
Production of the image, including at least one region of interest with its respective representation.

In conformity with another characteristic of the disclosure, the basic steps are repeatedly performed over time.

In conformity with another characteristic of the disclosure, at least one region of interest can be automatically defined when processing the data.

In conformity with another characteristic of the disclosure, at least one region of interest can be pre-defined.

In conformity with another characteristic of the disclosure, at least one region of interest can be defined by the user.

In conformity with another characteristic of the disclosure, at least one region of interest can be modified over time.

In conformity with another characteristic of the disclosure, the graphical representation of conditions, hazardous situations or trends in a region of interest can be done through the use of a color.

In conformity with another characteristic of the disclosure, the graphical representation of conditions, hazardous situations or trends in a region of interest can be achieved through the use of a texture such as, for example, a checkered or striped pattern, or lines with distinct thicknesses, etc.

In conformity with another characteristic of the disclosure, the graphical representation of conditions, hazardous situations or trends in a region of interest can be achieved through the use of a figure that may comprise, among others, an ellipse, an arrow, a collapsed alveolus, a hyperdistended alveolus, blocked artery, or traffic sign.

In conformity with another characteristic of the disclosure, the graphical representation of the region of interest may indicate the predominance of a certain condition in the region comprising, among others, atelectasis, hyperdistention, tidal recruitment, phase-shift ventilation, pulmonary shunt (perfusion without ventilation), dead spaces (ventilation without perfusion), dynamic pattern of abnormal ventilation, abnormal ventilation distribution, abnormal anatomy, pulmonary hypertension, volemic status, pulmonary resistance, or pulmonary compliance.

In conformity with another characteristic of the disclosure, the graphical representation of the region of interest may indicate the occurrence of an event in the region of interest, including, among others, pneumothorax, blockage, or selective intubation.

In conformity with another characteristic of the disclosure, the graphical representation of the region of interest may indicate a trend in the region, such as an increasing alveolar collapse.

In conformity with another characteristic of the disclosure, a region of interest is represented in a uniform manner, even encompassing pixels with different underlying impedance values.

In conformity with another characteristic of the disclosure, the graphical representation of the region of interest may suggest a procedure such as, among others, alveolar recruitment maneuver, patient's need for hydration, suggestion to adjust the artificial ventilator, or start or end of a weaning maneuver.

In conformity with another characteristic of the disclosure, a region of interest may be characterized through the combination of two or more graphical representations, which may be overlapped and simultaneously displayed, alternately displayed or displayed in order of priority.

In conformity with another characteristic of the disclosure, the proposed apparatus comprises an impedance tomography device that has a means to acquire the impedance signal, a means to process the data collected, a processing means to identify graphical representations for region of interest consisting of two or more pixels and a means to generate images, including at least one region of interest and its respective representation.

In conformity with another characteristic of the disclosure, the proposed apparatus may comprise a processing means to automatically define regions of interest, to store pre-defined ROIs and to allow users to define regions of interest.

In conformity with another characteristic of the disclosure, the proposed apparatus may comprise user interfaces to display, record, print and/or transmit data and images generated.

BRIEF DESCRIPTION OF THE DRAWINGS

The other characteristics and advantages of this disclosure will be more evident through the description of a preferred embodiment, given as example and not as limitation, and through the figures they refer to, wherein:

FIG. 6A shows a corresponding image of traditional EIT to emphasize the greater ease of interpreting an image by means of this disclosure. FIG. 6B schematically shows regions of interests and their respective representations, which indicate the occurrence of an event of selective intubation in the region.

FIG. 7A shows a corresponding image of traditional EIT to emphasize the greater ease of interpreting an image by means of this disclosure. FIG. 7B schematically shows regions of interest and their respective representations, which indicate the occurrence of an event of pneumothorax in a region.

DETAILED DESCRIPTION

In those cases requiring immediate medical intervention, it was found that the image simplification results in a benefit concerning interpretation and operation.

Accordingly, besides the indication of a pathological condition by a certain color or texture, the apparatus of the disclosure may indicate what should be done so that the affected region may again display the color that is considered normal.

Figure 5A:
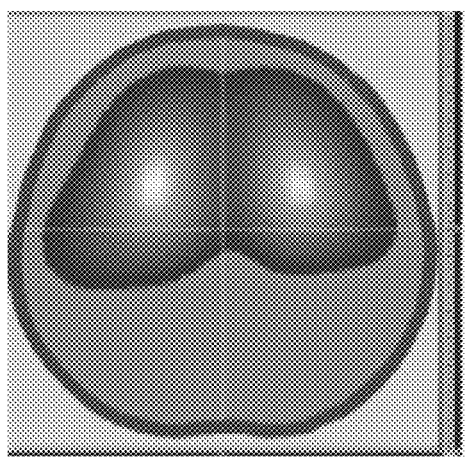
FIG. 5A shows a corresponding image of traditional EIT to emphasize the greater ease of interpreting an image by means of this disclosure.
Figure 5B:
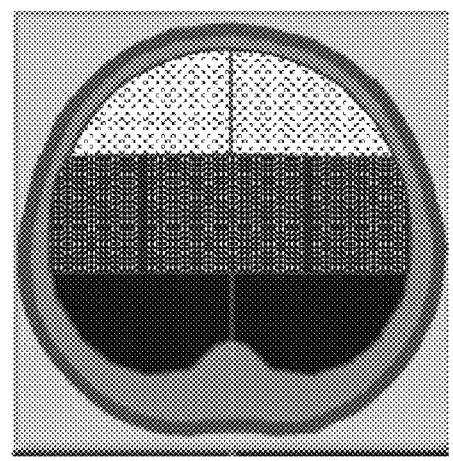
FIG. 5B schematically shows the definition of the region of interest that contains a set of two or more pixels. Moreover, graphical representations are determined for each region of interest, which indicates the predominance of a condition in this region, such as the collapse of the posterior part and the hyperdistention of the front part of the lung.
Figure 10:
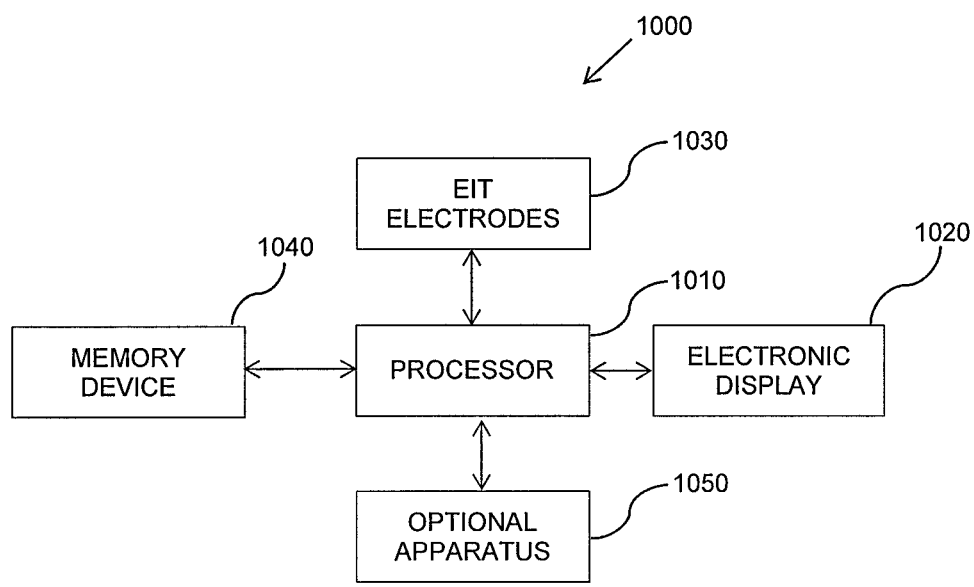
FIG. 10 is a simplified block diagram of an electrical impedance tomography (EIT) apparatus.

In conformity with this disclosure, the EIT apparatus 1000 (FIG. 10) is configured to perform algorithms that identify, for instance, the pixels whose respective alveoli are collapsing, causing atelectasis. Instead of displaying the image pixel by pixel, representing a specific alveolus as closely as possible as the aeration (or perfusion) state, the image is processed so as to indicate a major condition of certain regions of interest, as exemplified in FIG. 5B, simplifying both the identification of the approach to be adopted and, thus, the verification of the effectiveness of such clinical approach. As appropriate, note that a region of interest may contain pixels with different impedance values, and the region of interest in this case is defined by another condition considered preponderant and/or overriding.

Figure 8A:
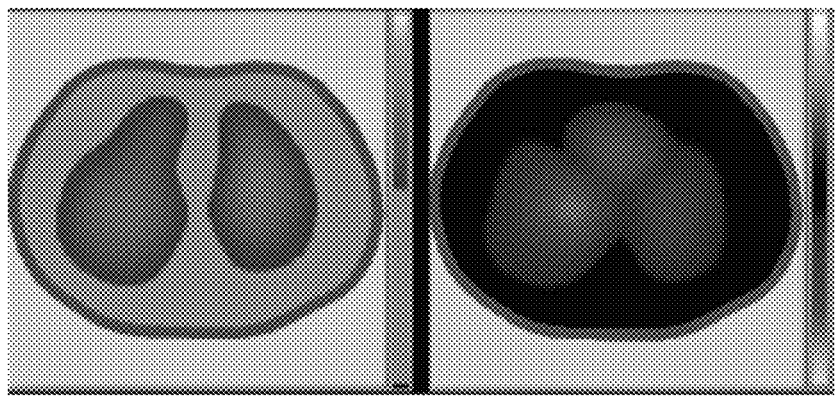
FIGS. 8A and 8B schematically show the combination of the representation of ventilation and hemodynamic for the same region. Instead of simply overlapping the images or displaying them side by side as shown in FIG. 8A, a checkered texture overlapped to a color is used in each of the regions of interest, as shown in FIG. 8B.
Figure 8B:
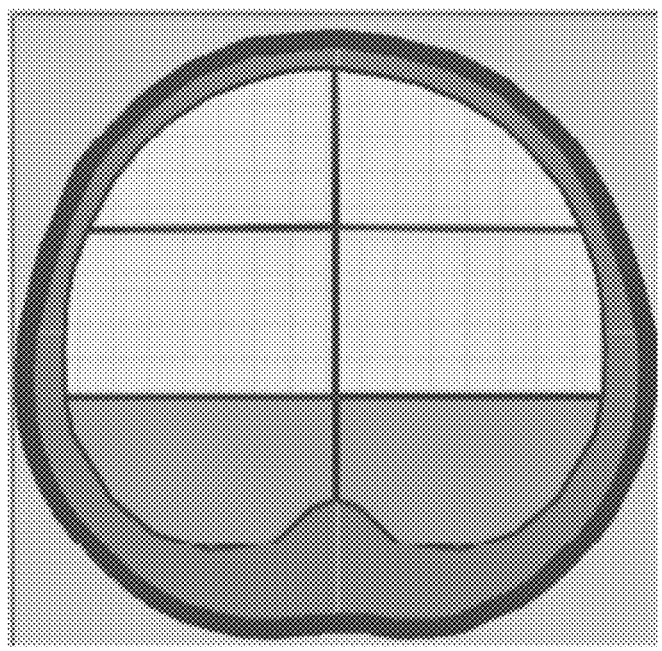
Figure 9:
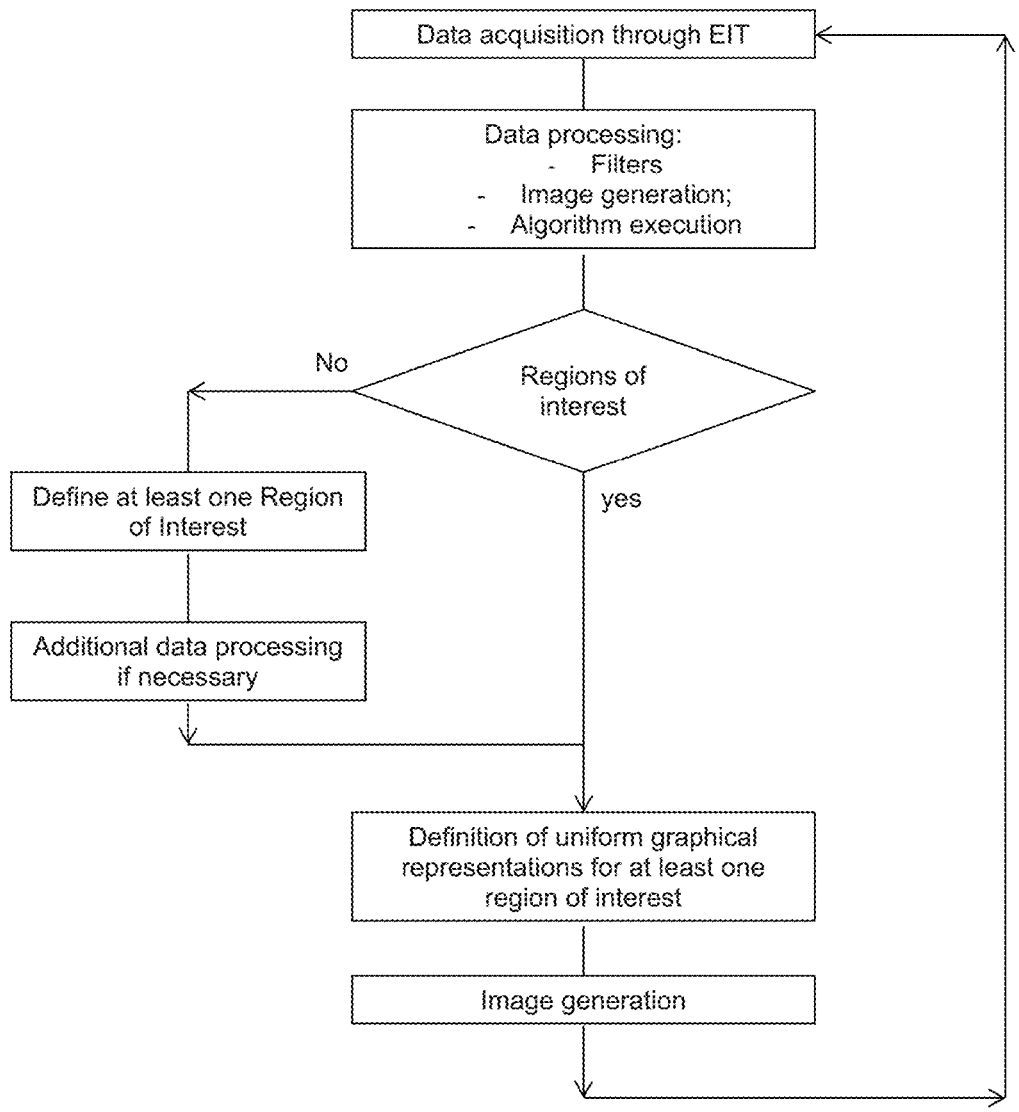
FIG. 9 schematically shows a flowchart with the basic steps of the method.

Several conditions, significant events and trends may simultaneously occur in a given region. The disclosure provides that each region may be displayed so as to simultaneously indicate its relevant conditions, events or trends. An illustrative way to do this is through the use of textures, colors and contour thickness, simultaneously displayed for each region of interest (see FIGS. 6B, 7B, and 8B).

Figure 1:
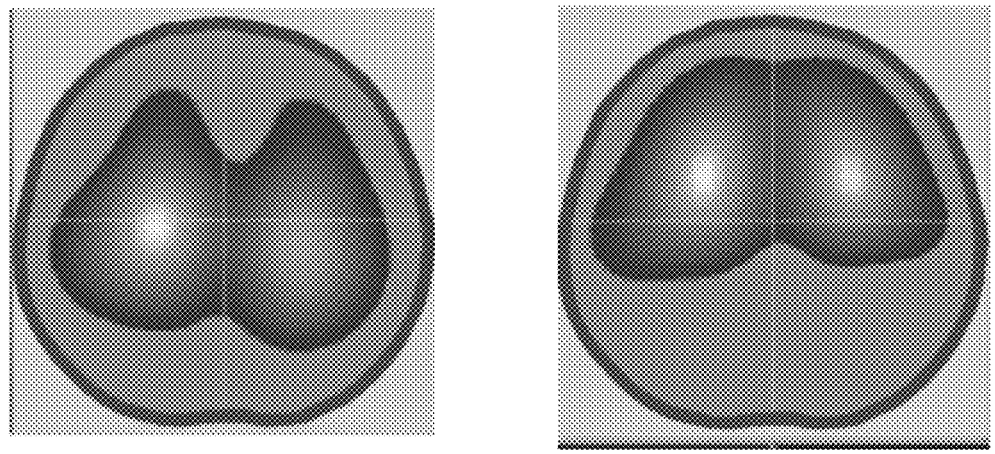
FIG. 1 schematically shows images displayed by the EIT apparatus, in conformity with the state of the art. The images are shown in their higher resolution, wherein the value of each pixel is calculated and displayed in conformity with a pre-determined color pattern.
Figure 2:
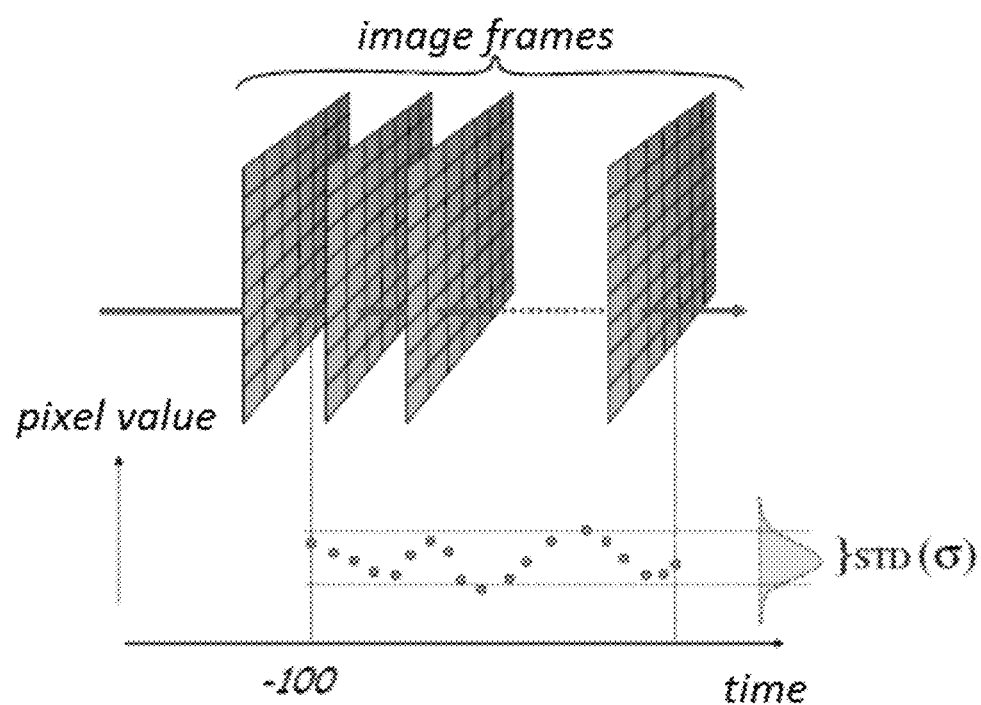
FIG. 2 schematically shows that, in conformity with the state of the art, graphs and other ways to simplify the information are drawn from the same data that generate the image. They are often shown on the side of the image, but they do not simplify the image itself.
Figure 3:
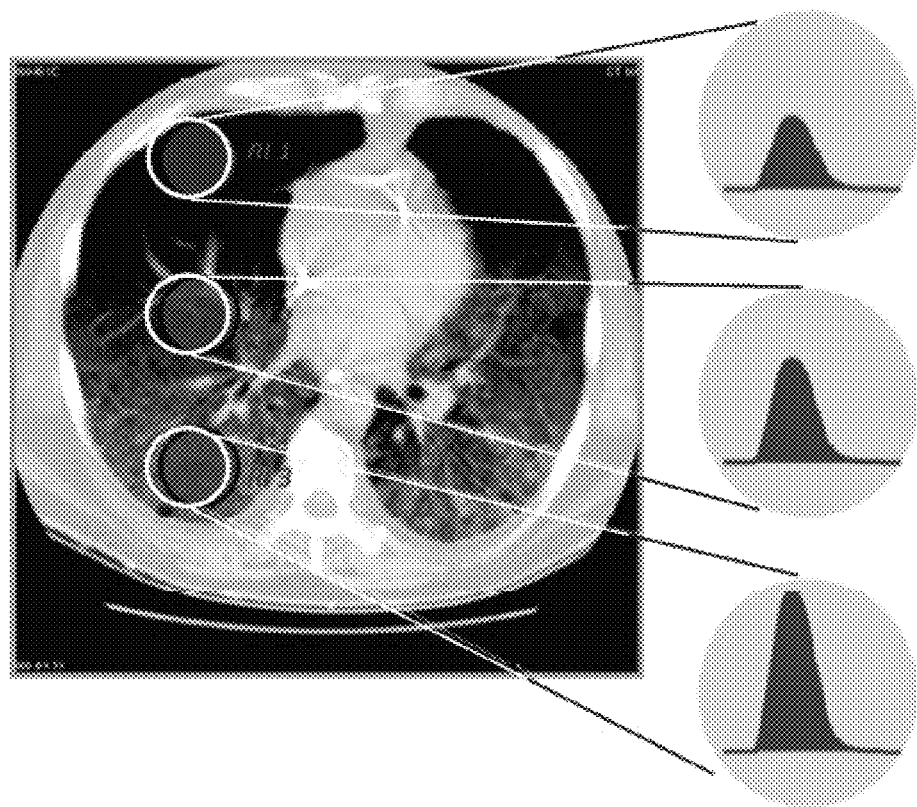
FIG. 3 schematically shows the concept of regions of interest (ROI), according to the prior art. In this figure, the circles delimit the three regions of interest selected and from these areas graphs are built and numerical values are drawn.
Figure 4:
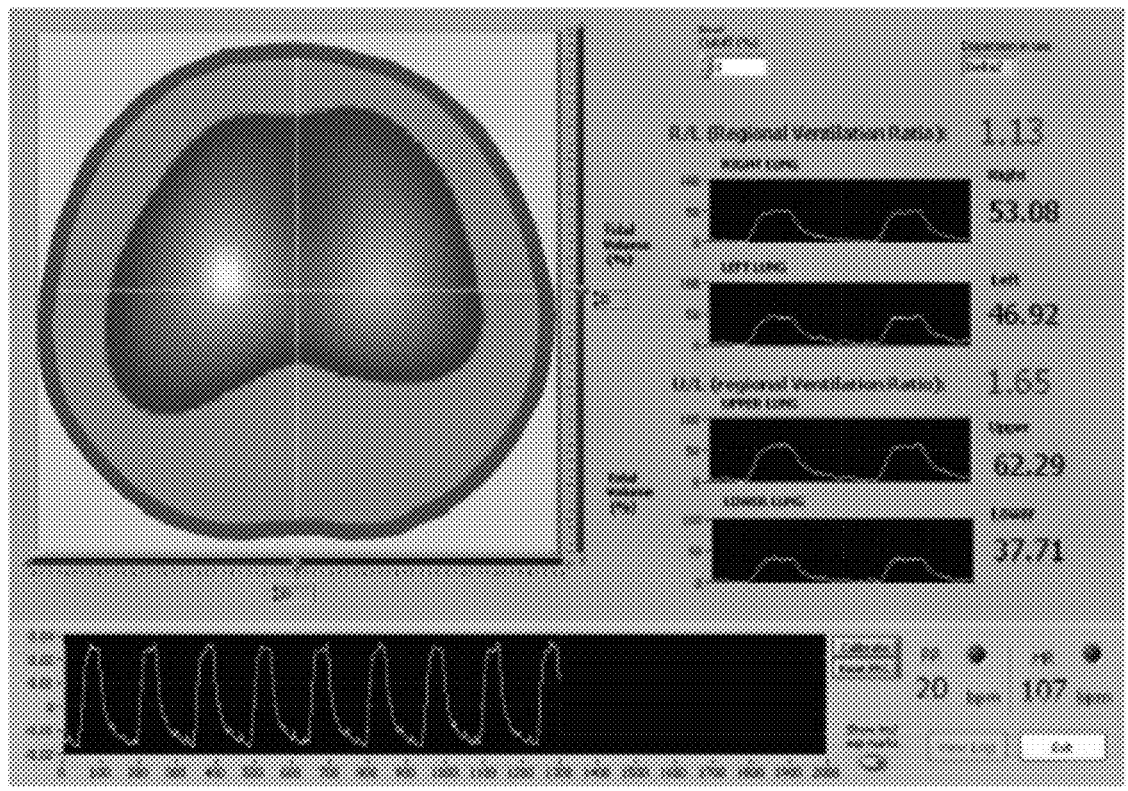
FIG. 4 schematically shows, in conformity with the prior art, the regions of interest defined from an image created through EIT. For each region of interest, graphs and numerical values are used so as to simplify the information to aid image interpretation. However, this approach involves a higher level of difficulty for the user as it adds a level to his/her cognitive process to interpret the information.

This disclosure simplifies the very image generated through EIT by determining the regions of interest and the graphical elements used to display each region. This is quite different from the prior art, in which information reducers are generated, such as graphs, along time or numerical values as shown in FIG. 2.

For a given set of data obtained through EIT, data processing is undergone and involves, for instance:
algorithms to identify collapse and hyperdistention,
algorithms to identify pneumothorax,
algorithms to detect ventilation distribution,
algorithms to detect shunt, dead space, etc., and
algorithms to determine the priority order of the identified or detected conditions.

Based on the results of these algorithms, the apparatus indicates possible areas of interest and suggests appropriate ways to display the results obtained by the application of the algorithms, simplifying the generated image itself.

Alternatively, the region of interest may be defined a priori, either through parameters stored (e.g., in memory device 1040 in FIG. 10) in the system, or through the introduction of criteria by a user. One or more of the algorithms are applied to define how each region must be displayed. Patient data, condition types and event types of greater interest also helps to redirect the priority and may be useful for data processing.

Algorithms are periodically applied to the collected data, in order to suggest new regions of interest, to update the representation of the current regions of interest, and even to detect events and, thus, displayed in a region of interest.

This process naturally culminates with a suggestion of diagnosis and/or procedure to be performed by the user, for instance, alveolar collapse suggesting a recruitment maneuver.

Thus, they constitute clinical decision support tools.

Ultimately, note that the image may be displayed in the EIT apparatus 1000 (e.g., via electronic display 1020 in FIG. 10) itself or in an apparatus (e.g., optional apparatus 1050 in FIG. 10) connected therewith. The analysis of the data can be performed by a processor (e.g., processor 1010) physically close to the circuit for signal acquisition, or even close to (or integrated into) other devices (e.g., optional apparatus 1050) to which the EIT can be integrated.

What is claimed is:

1. A method to generate and display a simplified representation of information obtained through electrical impedance tomography, the method comprising:
collecting electrical impedance tomography (EIT) data through operation of an electrical impedance tomography apparatus on a body;
processing the EIT data to detect one or more of a major condition, trend, or event therefrom;
defining at least one region of interest of a lung from the EIT data, the at least one region of interest comprising a set of two or more pixels determined to have in common the major condition, trend, or event detected from analyzing the EIT data, wherein at least some pixels of the set have different impedance values; and
generating and displaying a graphical representation of the lung of the EIT data on an electronic display, the graphical representation of the lung displayed with a common visual feature over the at least one region of interest that overrides display of impedance information of each individual pixel within the at least one region of interest.

2. The method of claim 1, wherein processing the EIT data includes processing the EIT data directly or processing data derived from the EIT data.

3. The method of claim 1, wherein steps of collecting, processing, and defining are repeated over time to update the graphical representation.

4. The method of claim 1, wherein the at least one region of interest is automatically defined responsive to data being processed.

5. The method of claim 1, wherein the at least one region of interest is pre-defined.

6. The method of claim 1, wherein the at least one region of interest is defined by the user.

7. The method of claim 1, wherein the at least one region of interest is modified over time.

8. The method of claim 1, wherein the common visual feature includes one or more of a common:
- color;
- texture;
- figure; or
- contours outlining the at least one region of interest.

9. The method of claim 1, wherein processing the EIT data includes detecting predominance of the major condition selected from the group consisting of atelectasis, hyperdistention, tidal recruitment, phase-shift ventilation, pulmonary shunt, dead spaces, abnormal dynamic pattern of ventilation, abnormal ventilation distribution, abnormal anatomy, pulmonary hypertension, abnormal volemic status (high or low), pulmonary resistance, and pulmonary compliance.

10. The method of claim 1, wherein processing the EIT data includes detecting an occurrence of an event in the at least one region of interest, wherein the event is selected from the group consisting of pneumothorax, blockage, and selective intubation.

11. The method of claim 1, wherein processing the EIT data includes detecting a trend in the at least one region of interest, wherein the trend includes an increasing alveolar collapse.

12. The method of claim 1, further comprising displaying a suggested procedure with the graphical representation, the suggested procedure selected from the group consisting of an alveolar recruitment maneuver, adjustment of an artificial ventilator, patient hydration, and a weaning maneuver.

13. The method of claim 8, wherein displaying the graphical representation of at least one region of interest of the lung includes displaying a combination of two or more visual features corresponding to different conditions, events or trends.

14. The method of claim 13, wherein the two or more visual features are overlapped and simultaneously displayed within the at least one region of interest of the graphical representation of the lung.

15. The method of claim 13, wherein the two or more graphical features are alternately displayed within the graphical representation of the lung.

16. The method of claim 13, wherein the two or more graphical features are displayed within the graphical representation of the lung in order of priority for the different conditions, events, or trends detected.

17. An apparatus to simplify information obtained through electrical impedance tomography, the apparatus comprising:
- an electrical impedance tomography (EIT) apparatus configured to acquire an impedance signal as EIT data;
- an electronic display;
- a processor operably coupled with the EIT apparatus and the electronic display, and configured to:
  - define at least one region of interest responsive to processing the EIT data, each region of interest including two or more pixels having a common major condition, trend, or event; and
  - generate and display output images of a lung on the electronic display including overriding the impedance information of the two or more pixels within the at least one region of interest with a graphical representation that is substantially uniform visually including for pixels within the at least one region of interest having different underlying impedance values.

18. The apparatus of claim 17, further comprising at least one of the following elements:
- a device configured to record the generated output images;
- a transmitter configured to transmit the generated output images;
- a printer configured to print the generated output images;
- a user interface configured to enable a user to define regions of interest; or
- a memory device configured to store the regions of interest.

19. The apparatus of claim 17, wherein the graphical representation is substantially uniform visually according to one or more of a color, a texture, a figure, or a contour outlining the two or more pixels of the at least one region of interest.

* * * * *